(12) United States Patent
Homola (10) Patent No.: US 6,180,065 B1
(45) Date of Patent: Jan. 30, 2001

(54) MULTICHANNEL DILUTION RESERVOIR (75) Inventor: Margit E. Homola, Morgan Hill, CA (US)

(73) Assignee: Dilux, Inc., Morgan Hill, CA (US)

( * ) Notice: Under 35 U.S.C. 154(b), the term of this patent shall be extended for 0 days.

(21) Appl. No.: 09/155,699

(22) PCT Filed: Jun. 5, 1997

(86) PCT No.: PCT/US97/10068

§ 371 Date: Oct. 5, 1998

§ 102(e) Date: Oct. 5, 1998

(87) PCT Pub. No.: WO97/47388

PCT Pub. Date: Dec. 18, 1997

Related U.S. Application Data (60) Provisional application No. 60/019,609, filed on Jun. 11, 1996.

(51) Int. Cl.[7] .................................................. B01L 3/02
(52) U.S. Cl. ........................... 422/102; 422/99; 422/100; 422/104; 435/288.4; 435/305.2; 435/305.3
(58) Field of Search ............................. 422/99, 100, 102, 422/104, 915, 916, 917, 944, 945; 435/288.3, 288.4, 305.2, 305.3

(56) References Cited

U.S. PATENT DOCUMENTS

| | | |
|---|---|---|
| 3,505,023 | 4/1970 | Van Damme . |
| 3,533,744 | 10/1970 | Unger . |
| 3,547,781 | 12/1970 | Guigan et al. . |
| 3,692,498 | 9/1972 | Frank et al. . |
| 4,031,197 * | 6/1977 | Marinkovich ............................. 424/1 |
| 4,503,011 * | 3/1985 | Hubeau ................................... 422/73 |
| 4,661,460 * | 4/1987 | Sakuma ................................ 436/165 |
| 4,728,504 * | 3/1988 | Nichols ................................. 422/297 |
| 4,828,801 * | 5/1989 | Lombardy et al. ................... 422/102 |
| 4,968,625 * | 11/1990 | Smith et al. .......................... 435/301 |

* cited by examiner

Primary Examiner—Jeffrey Snay
Assistant Examiner—Patricia Kathryn Bex
(74) Attorney, Agent, or Firm—Hickman Coleman & Hughes, LLP (57) ABSTRACT

A dilution reservoir (10) with one or more channels (30) is provided in which the channels (30) are easily accessible and which allow improved material manipulation. The dilution reservoir (10) includes a housing (14), having a base (18), a top (16) opposite the base (18) and a plurality of sides (20), (22). One or more channels (30) are located in said housing (14), each channel (30) having a mouth (40) at the top (16) of the housing (14) which opens into a cavity (38). Each channel (30) and each cavity (38) has a longitudinal axis (44), a transverse axis (48), a depth axis (46), and the channels (30) have arcuate cross-sections. These arcuate cross-sections provide true low points (60) in the bottom (56) of each cavity (38) which facilitate collection of material. The mouths (40) of the channels (30) are elongated in the direction of the longitudinal axis (44) thus allowing a wider range of access angles (78) for insertion of a standard pipettor. The dilution reservoirs (10) have channels (30) which may be grouped in multiples of 3, 4 or 6. The dilution reservoirs (10) may be stackable to facilitate storage and may be disposable to promote sterility and to avoid contamination. The dilution reservoirs (10) are provided with an optional cover (12) to prevent spillage and evaporation of volatile materials.

13 Claims, 5 Drawing Sheets

MULTICHANNEL DILUTION RESERVOIR

This application claims the benefit of U.S. Provisional Application Ser. No. 60/019,609, titled DISPOSABLE MULTICHANNEL DILUTION RESERVOIR, by Margit E. Homola, filed on Jun. 11, 1996, and which is hereby incorporated by reference in its entirety.

TECHNICAL FIELD

The present invention relates generally to labware used for the preparation of samples and reagents in chemical and biological laboratories, and more particularly to multicavity dilution reservoirs for such use.

BACKGROUND ART

A variety of vessels have been employed in research facilities and medical clinics for the manipulation of material samples. In the biotechnology industry, these types of vessels are standardly referred to as "dilution reservoirs", although these vessels are commonly used for numerous other purposes besides preparing sample and reagent dilutions.

Generally, these can be categorized as being either trough or well type dilution reservoirs. The most basic example of the well type of reservoir is the well-known test tube, which is generally characterized by having a small mouth opening and a long straight neck. The test tube is generally configured to be symmetrical about a central longitudinal axis. The traditional test tube was generally filled by use of a single pipette or squeeze-bulb dropper.

The development of multichannel pipettors allows filling of multiple reservoirs from a single pipettor (also frequently spelled "pipetter"). These usually consist of a parallel array of thin tubes or pipettes controlled by a common handle which can draw and dispense multiple samples of material. Such pipettors typically come with eight or twelve channels and have dispensing tips centered approximately 9mm apart, according to industry standards. Typical industry examples of multichannel pipettors include Finnpippete, T/M; Eppendorf, T/M; Oxford BenchMate, T/M; and Fisher/Wheaton Calibra, T/M.

In response to the development of these multichannel pipettors, systems or arrays of well dilution reservoirs have been made, with rows of tubes bound together in multiples of eight or twelve wells. They may also be formed with square-shaped cross-sections in which the wells may share walls with their neighbors. The individual wells must be reduced in size in order to accommodate the 9mm spacing dimensions of the pipettor tips, thus generally the volumetric capacity of such wells is small unless the depth is increased to an awkward length. Industry examples of well systems designed for use with multichannel pipettors include Corning Well ELISA Plates and Strips, T/M, and Bel-Art Products Mini-Tubes, T/M.

Well type dilution reservoirs have a natural ergonomic disadvantage. In order to dispense material from the multichannel pipettor, the tips of the pipettor channels must be inserted into the relatively small mouths of the well channels, in unison, from a nearly vertical orientation. This can require a very steady hand, and upon repetition, this can become tiring and over lengths of time can lead to complaints of repetitive stress problems such as carpal-tunnel syndrome. Chances of spillage are also increased as the target areas for the pipettor tips are relatively small.

Well dilution reservoirs also have generally small volumetric capacity, as mentioned above, as often as small as 50–250 micro-liters. This small capacity may impede effective mixing of materials if stirring apparatus is difficult to introduce into the cavity, if range of motion of this apparatus is too restricted, or if introduction of stirring apparatus causes concerns of material overflow due to volumetric displacement in these small capacity tubes.

Trough type dilution reservoirs, as the name implies, usually have elongated mouths which have greater length than width. The trough cavities can thus be thought of as having a longitudinal axis, parallel to the length dimension of the mouths and a transverse axis, parallel to the width of the mouths. These trough reservoirs generally provide greater volumetric capacity than the well type reservoirs. There are single reservoirs which can have very large capacities such as 100 milliliters. Trough reservoirs can also have smaller channels which have been grouped together in arrays of eight or twelve, corresponding to pipettor channel configuration. The center to center spacing of the trough mouths may accommodate the standard 9 mm spacing of the multichannel pipettor dispensing tips in a similar way to the arrays of well reservoirs. However, the troughs allow insertion of the pipettor from a greater range of non-vertical approach angles, thus providing an ergonomic advantage over the well type reservoir.

Troughs also have advantages over wells when mixing materials. If mixing is done in a trough prior to distribution to an array of well reservoirs, higher accuracy and precision may be achieved compared to mixing which is done in an array of well reservoirs in which a multichannel pipettor is used to add and then mix materials in the wells themselves. Especially in small volume well reservoirs, small factors such as the presence of bubbles in the pipettor can introduce errors in mixture concentrations. When dealing with small volumes, such errors can more easily constitute a significant percentage of the overall mixture, compared to large volumes of mixture. Small errors introduced into a larger volume mixture may be distributed among the samples, thus making up a smaller, less significant percentage of the overall mixture.

Examples of standard industry trough type reservoirs include Matrix Reagent Reservoirs, T/M; Fisher Multichannel Pipetter Basins, T/M; and E & K Disposable Pipettor Basins, T/M.

Unfortunately, despite the advantages of the trough type dilution reservoir over the well type dilution reservoir, there remain some disadvantages. In applications where very precise quantities of material are to be transferred into and then out of a dilution reservoir, it can be of critical importance that the reservoir contents be capable of complete removal, leaving minimal residue in the reservoir. It is thus important that the reservoir be designed for easy and complete withdrawal of the contents. Previous trough dilution reservoirs often had flat bottoms with no true low point for collection of the contents. Some trough type reservoirs have bottoms which are rounded in a cross-sectional view taken through the cavities' transverse axes, but which are flat as seen in a cross-sectional view through their longitudinal axes. The material will thus tend to accumulate in a line in the bottoms of the cavities along the longitudinal axes. This will make collection of material difficult, as a withdrawal device will need to sweep along this line to collect all the material.

A few previous trough type reservoirs have a low collection point near one end of the elongated mouth, which could facilitate material removal. However, this placement restricts the angle at which this low point can be approached with the pipettor.

Some laboratories perform many material manipulations in the course of a day. This necessitates the use of many dilution reservoirs, which must be either thoroughly cleaned before reuse, or discarded to prevent possibility of contamination of subsequent material. Especially in uses where biological samples are manipulated, sterility of the reservoirs can be a great concern. Disposable reservoirs thus have advantages, as they can be maintained in a sterile condition until use and then discarded.

For reservoirs which are not disposable, choice of material for the unit's composition is very important. A preferred material would have the characteristics of being very inert in contact with biological materials, would have low affinity for sticking or binding of proteins and other materials, and would be easy to sterilize by autoclave or radiation sterilization. Virgin medical grade polypropylene has all of these qualities, and is additionally optically transparent so that a user can readily determine the amount of material in the reservoir.

The high numerical usage of dilution reservoirs in laboratories can make storage space a concern. Thus it will be advantageous if the reservoirs are made to be stackable, thus reducing volume during shipping, for storage before use in the laboratory and for disposal after they have been used.

An optional cover helps to prevent spillage, evaporation of volatile materials, and avoids contamination of reservoir contents.

There is thus a great need for a trough type dilution reservoir which holds enough volume to allow easy mixing of material, is configured with multiple channels which are accessible by multichannel pipettors, allows complete and easily accessible removal of the contents, and is designed for easy ergonomic manipulation of the reservoir material. The reservoir could be even more useful if made to be disposable and stackable, with an optional cover.

DISCLOSURE OF THE INVENTION

Accordingly, it is an object of the invention to provide a multichannel dilution reservoir that allows easy ergonomic pipettor access.

It is another object of the invention to provide a multichannel dilution reservoir that facilitates material manipulations in relatively large volumes.

It is also an object to provide a multichannel dilution reservoir that retains uniform sizing and centering of cavity mouths to accept standard multichannel pipettors.

It is yet another object to provide a multichannel dilution reservoir that provides efficient dispensing and removal of liquids.

It is a further object to provide a multichannel dilution reservoir that facilitates easy and rapid mixing of liquid contents.

It is still another object to provide a multichannel dilution reservoir that promotes easy and complete withdrawal of reservoir contents.

It is a yet further object to provide a multichannel dilution reservoir that is easily stackable.

It is a still further object to provide a multichannel dilution reservoir that is disposable, thus maintaining sterilization and preventing contamination.

It is also a further object to provide a multichannel dilution reservoir that is made of material that is bio-inert, has low bio-affinity so that material will not stick to it, and which may be optically transparent.

It is also a still further object to provide a multichannel dilution reservoir that has an optional removable cover to prevent spillage, evaporation, and contamination of contents.

Briefly, one preferred embodiment of the present invention is a disposable multichannel dilution reservoir which is optionally stackable, having channels with an arcuate cross-section, and an optional removable cover. The dilution reservoir includes a housing having a base with an optional flared extension to provide stability, a top surface which provides space for optional informational markings and four sides. The dilution reservoir may have 3, 4, 6, 8, 12 or another number of channels, each channel being separated from its neighbor by a thin wall. Each channel includes a cavity and has a mouth for introduction of material into the cavity. The channels are of an appropriate size and spacing to allow insertion of a standard multichannel pipettor and have a large range of access angles which allow easy ergonomic pipettor access. Each channel also has a low point in its bottom which facilitates complete withdrawal of material from the cavities.

An advantage of the present invention is that the individual reservoir cavities contain a relatively large volume which facilitates easy and rapid mixing of materials.

Another advantage of the invention is that each channel is formed with a low point that promotes easy and complete withdrawal of reservoir contents.

Yet another advantage of the invention is that the reservoir retains uniform sizing and centering of channel mouths to accept standard multichannel pipettors.

It is a still further advantage of the invention that the cavities have a large range of access angles which allow for ergonomically easy insertion of a multichannel pipettor.

Still another advantage of the invention is that the multichannel dilution reservoirs are easily stackable.

A yet further advantage of the present invention is that the reservoirs are disposable, to more easily maintain sterility and prevent contamination.

Also, the present invention has the advantage that it can be made from material which is bio-inert, has low bio-affinity and which may be optically transparent.

It is also a further advantage that the invention has an optional removable cover to prevent spillage and evaporation, and to avoid contamination of contents.

These and other objects and advantages of the present invention will become clear to those skilled in the art in view of the description of the best presently known mode of carrying out the invention and the industrial applicability of the preferred embodiment as described herein and as illustrated in the several figures of the drawings.

BRIEF DESCRIPTION OF THE DRAWINGS

The purposes and advantages of the present invention will be apparent from the following detailed description in conjunction with the appended drawings in which:

FIG. 3 is a view of the invention taken along cross-section 1—1 of FIG. 1, while

FIG. 7a is a major axis side cross-sectional view of the inventive multichannel dilution reservoir, while

BEST MODE FOR CARRYING OUT THE INVENTION

A preferred embodiment of the present invention is a multicavity dilution reservoir. The term "dilution reservoir" is an industry standard for the generic class of containers to which the present invention belongs. Accordingly, that term will be used herein. However, it should be appreciated that industry makes numerous other uses beside sample and reagent dilution for such containers, and the inventor fully expects this invention to find similar general acceptance and application for both dilution and non-dilution tasks.

Figure 1:
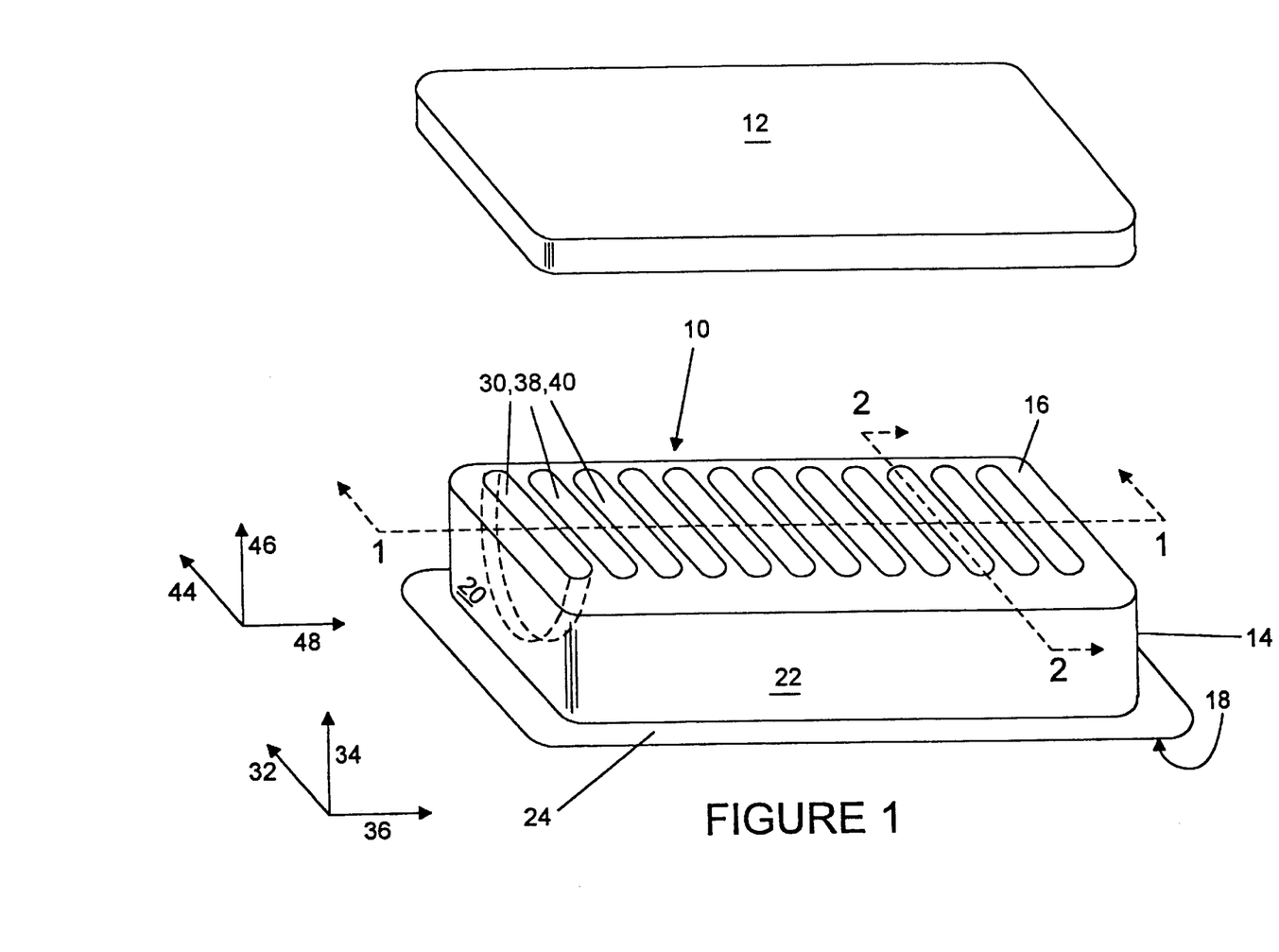
FIG. 1 is a perspective view of a preferred embodiment of the invention and its optional cover.

As illustrated in the various drawings herein, and particularly in the view of FIG. 1, a form of this preferred embodiment of the inventive device is depicted by the general reference character 10. Further, an optional cover 12 may be provided, to reduce evaporation and prevent contamination of samples stored in the dilution reservoir 10.

FIG. 1 illustrates a preferred embodiment of the dilution reservoir 10 in perspective view. Included is a roughly block rectangular shaped housing 14, having a top surface 16, a base 18 (opposite the top surface 16, and not readily visible in FIG. 1), two narrow sides 20, and two long sides 22. In the preferred embodiment an optional flared extension 24 is provided at the base 18, which provides added stability for the dilution reservoir 10 when it is set upon a surface such as a laboratory table or a storage shelf. For discussion, the dilution reservoir 10 can be defined as having three axes which will here be termed a length axis 36 (i.e., an x-axis), a height axis 34 (i.e., a y-axis), and a width axis 32 (i.e., a z-axis in a Cartesian coordinate system).

Figure 2:
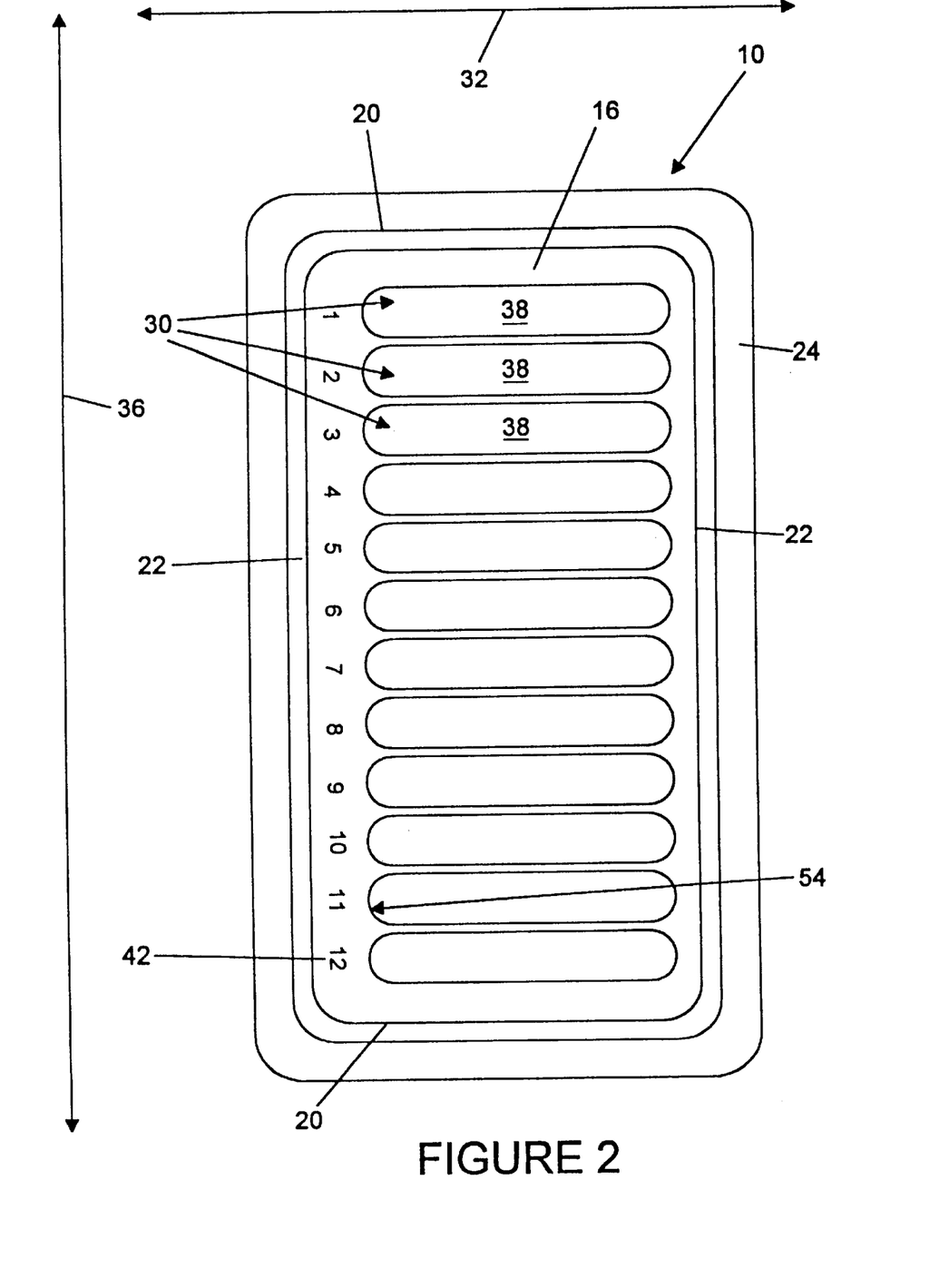
FIG. 2 is a top plan view of the invention.
Figure 3:
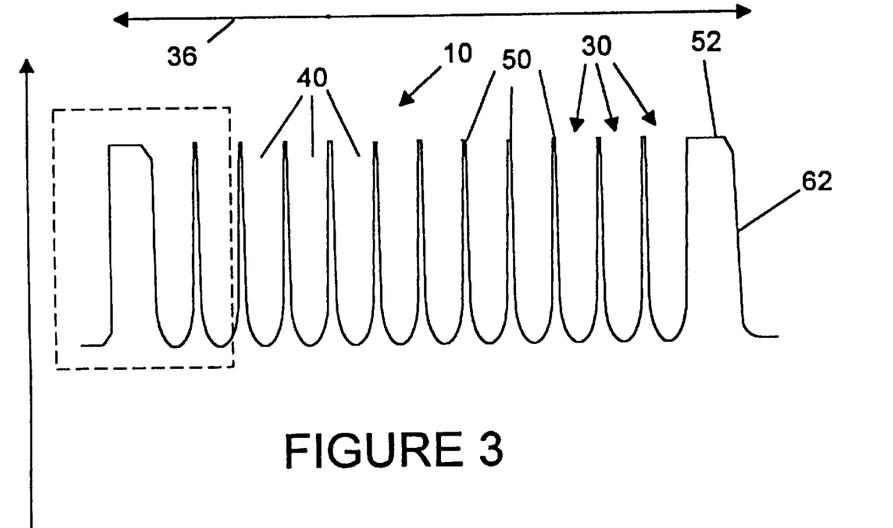
Figure 3A:
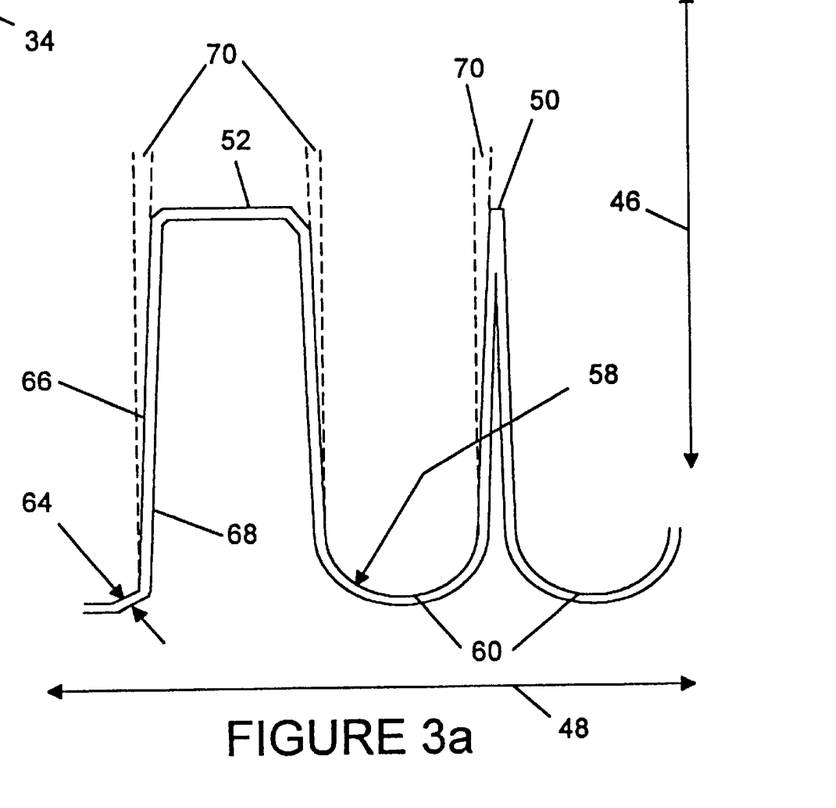
FIG. 3a is an enlarged view of the left end region of FIG. 3.

The primary feature of the dilution reservoir 10 is a number of channels 30 having cavities 38 which provide large volumetric capacity for liquid contents stored in the dilution reservoir 10. Each cavity 38 (FIG. 2) opens at the top surface 16 of the housing 14 at a mouth 40. The cavities 38 are spaced apart perpendicular to the length axis 36, but not necessarily centered between the long sides 22 on the top surface 16. For example, in the figures the cavities 38 are shown offset as a group toward one of the long sides 22 of the housing 14, thus providing room on the top surface 16 of the housing 14 for optional informational marking 42, which may be specific to individual cavities 38 (e.g., an identifying number or character for each cavity 38). For discussion, both the channels 30 and the individual cavities 38 can be defined as also having three axes which will here be termed a longitudinal axis 44, corresponding to the width axis 32; a depth axis 46, corresponding to the height axis 34; and a transverse axis 48, corresponding to the length axis 36. Separating each pair of cavities 38 is a central barrier 50, and separating each narrow side 20 of the housing 14 from the proximate cavity 38 is an end barrier 52 (FIGS. 3 and 3a).

Sides of the cavities 38 which cross the longitudinal axis 44 (i.e., at the ends of the trough shapes of the cavities 38) are formed with generally rounded or arcuate shaped sides 54 (FIG. 2) and bottoms 56 and 58 (FIGS. 3, 3a, and 4; i.e., rounded in multiple dimensions) which form a low point 60 in each cavity 38, to permit easy withdrawal of liquid samples stored in the dilution reservoir 10. However, it should be appreciated that other shapes may also be suitable (e.g., straight sloping sides, but such would reduce volumetric capacity). As can be appreciated from the figures, a preferred shape for the cavities 38 is generally crescent, half-circle, or semi-circular. This choice of shape is intentionally made to facilitate stacking of dilution reservoirs 10 as well as draining of liquid contents of the dilution reservoir 10 to the low points 60, for easy and rapid mixing of liquid contents (e.g., reagents) and for easy and complete withdrawal of dilution reservoir 10 contents.

The inventor's preferred embodiment of the dilution reservoir 10 is manufactured as a single piece unit in which the housing 14 provides stable support for the cavities 38, to facilitate easy delivery and removal access to contents as well as stable and level liquid storage. As previously noted, a cover 12 unit may be optionally provided. In the inventor's preferred embodiment, the dilution reservoir 10 is formed by injection molding into a single wall 62 of generally consistent thickness 64 (e.g., 0.8 mm), having an upper surface 66 and a lower surface 68. This thickness and the method of manufacture can, of course, be varied with material and as structural needs change with various implementations of the invention. The preferred material for all parts of the invention is virgin medical grade polypropylene known for its bio-inertness, low affinity for biological materials (e.g., proteins stick or bind very poorly), ease of sterilization (e.g., by autoclaving and radiation sterilization), and relative optical transparency (a user can readily visually determine if a cavity 38 has contents, and in roughly what amount). Other materials can, of course, be substituted (e.g., polystyrene). When made in the above manner, minimal material is required for the dilution reservoir 10 or its optional cover 12, thus reducing materials cost, unit weight, and disposal mass (notably making compacting easy as part of the disposal process).

Due to concerns about maintaining sterilization, preventing contamination, and satisfying the numerically high demand for dilution reservoirs in typical laboratory settings today (a major anticipated market), the inventor has tailored the preferred embodiment to be both disposable and insertably stackable. However, it should be noted that neither of these features are necessary to the spirit of the present invention. For example, the dilution reservoir 10 can easily be made with the housing 14 as a filled-in solid, say to promote maximum stability, but this would also discourage disposal and would require greater volume for stacked storage.

Figure 4:
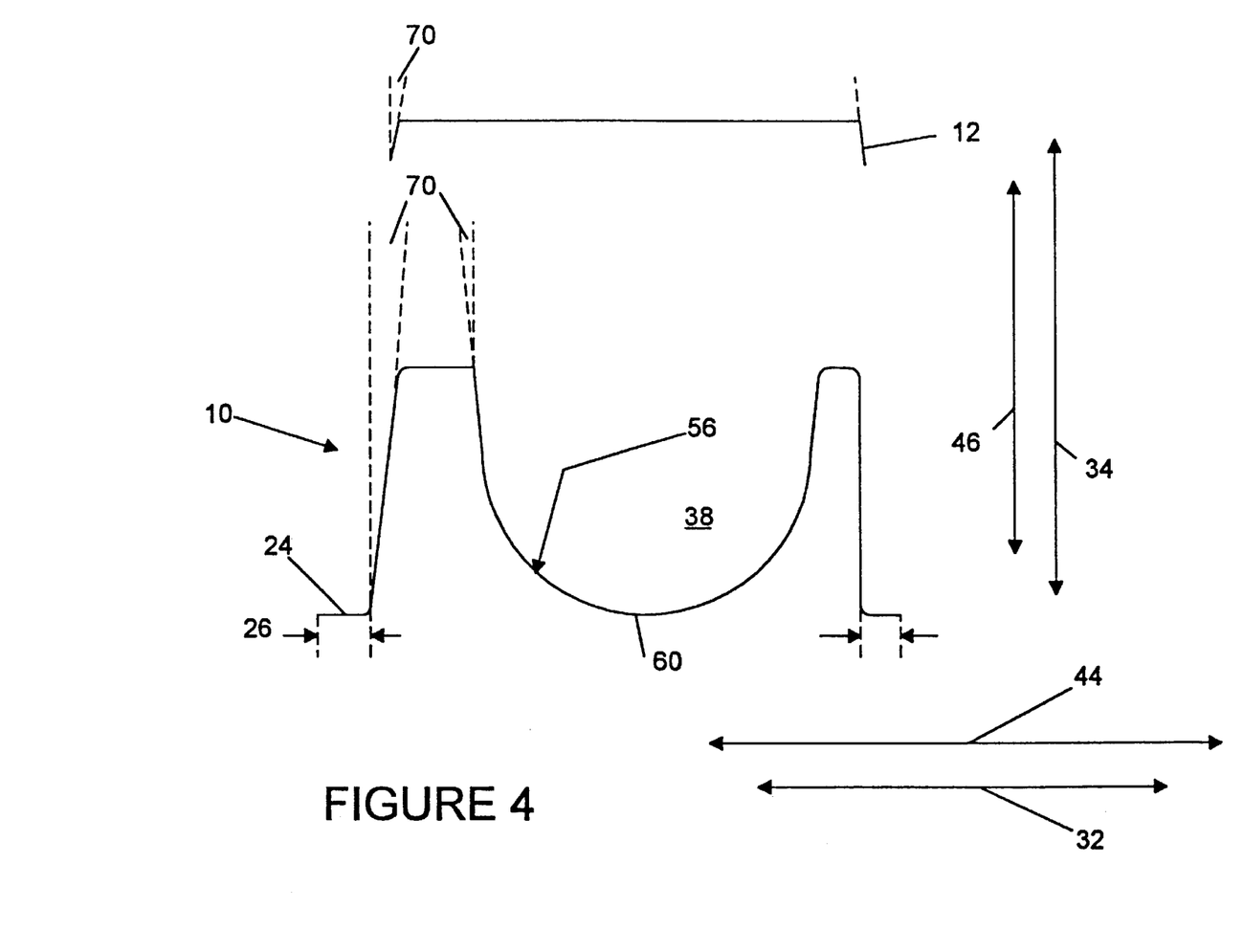
FIG. 4 is a view of the invention and its cover taken along cross-section 2—2 of FIG. 1.

The feature of insertable stacking of the invention is accomplished by suitable choice of the overall shapes of both the dilution reservoir 10 and cover 12, as well as individual features such as the cavities 38, by tapering the dimensions of the device, much in the manner of other common liquid containers when empty (e.g., disposable coffee cups and lids). FIGS. 3, 3a, and 4 illustrate various taper angles 70 of the wall 62 at various points to accomplish this in the preferred embodiment. The precise details of the stackability promoting dimensions of the various embodiments of the invention are not germane to the spirit of the invention and will not be belabored here, since engineering for insertable stackability generally is already a well known art.

In the figures, twelve channels 30 are depicted. However, this number is not necessary, and dilution reservoirs 10 having three, four and six channels 30 are anticipated by the inventor to be commonly marketed alternates. (It should be noted that in the case of an embodiment having four channels which are the same size as those depicted in the figures here, the short sides 20 and the long sides 22 of the housing 14 may not necessarily be "short" and "long" in relative relationship.) Further, while the channels 30 shown in the figures here all have one consistent size, this also is not a requirement. For example, specialized embodiments may be made with one or more larger channels 30 by eliminating one or more of the central barriers 50. In this manner dilution reservoirs 10 having the same major housing 14 dimensions as those of the embodiment shown in the figures can be made, but having six double sized or four triple sized channels 30, or even combinations of channel 30 sizes.

A key feature which the inventor anticipates will be provided in most embodiments of the dilution reservoir 10 is uniform sizing and centering of the mouths 40 of the channels 30 to accept liquids dispensed from industry standard multichannel pipettors (also frequently spelled "pipetter"). Such pipettors typically come with either eight or twelve channels, and have dispensing tips centered roughly 9 mm apart. Standard industry examples include Finnpipette, T/M; Eppendorf, T/M; Oxford BenchMate, T/M; Fisher/Wheaton Calibra, T/M; and others. This feature of the invention optimizes multichannel pipetting by providing rapid, easy, and ergonomic pipettor content dispensing (i.e., dilution reservoir 10 filling).

It should particularly be noted that providing both efficient dispensing and removal of liquid contents, and particularly facilitating preparation of sample dilutions and reagents in relatively large volumes are key distinctions of the inventive dilution reservoir 10 from the prior art. The prior art can, roughly, be categorized as consisting of well and trough type dilution reservoirs. Well systems resemble racks of conventional test tubes, reduced in size to accept pipettor delivery. Like test tubes, wells have approximately the same cross-section in both the x-axis and z-axis. Typical industry examples of well systems for use with pipettors include Corning Well ELISA Plates and Strips, T/M; and Bel-Art Products Mini-Tubes, T/M. Unfortunately, wells tend to have limited volumetric capacity, unless the depth is increased to an awkward length. Wells also tend to be non-ergonomic, since insertion of content delivery devices (e.g., pipettors) must be near vertical, and thus require a very steady hand.

Increasing dilution reservoir volumetric capacity and providing ergonomic pipettor access are two reasons for using a trough type dilution reservoir (i.e., one having cavities with non-equal x-axis and z-axis dimensions). Troughs provide a more ergonomic form for access with pipettors because they have a wider range of possible approach angles.

Figure 5A:
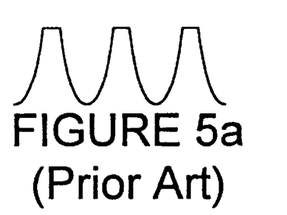
FIG. 5a (prior art) is a major axis side cross-sectional view of a typical prior art multichannel dilution reservoir, while FIG. 5b (prior art) is a minor axis side cross-sectional view of this reservoir.
Figure 5B:
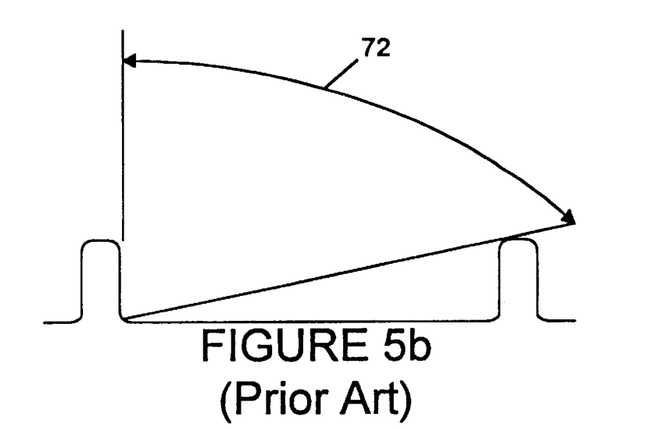
Figure 6A:
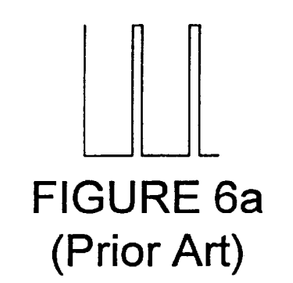
FIG. 6a (prior art) is a major axis side cross-sectional view of another typical prior art multichannel dilution reservoir, while FIG. 6b (prior art) is a minor axis side cross-sectional view of this reservoir.
Figure 6B:
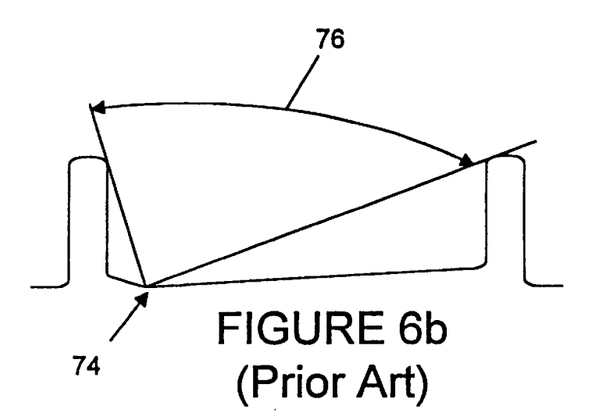

FIGS. 5*a–b* (prior art) respectively illustrate a multichannel trough system in x-y and z-y cross-sections, with a delivery/removal access angle range 72 shown in FIG. 5*b*. Notably, this type of prior art dilution reservoir has no single low point for liquid to collect at under the influence of gravity. Additionally, this type of prior art reservoir has very shallow troughs which present a significant danger of spillage. FIGS. 6*a–b* (prior art; again depicting x-y and z-y cross-sections) is an improvement over the dilution reservoir of FIGS. 5*a–b* because this dilution reservoir does provide a low end 74.

Figure 7A:
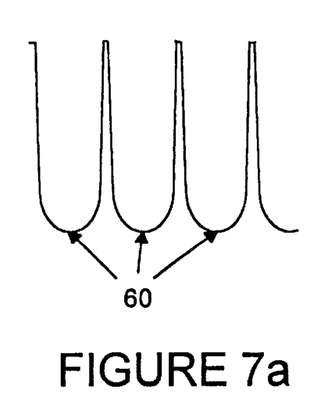
Figure 7B:
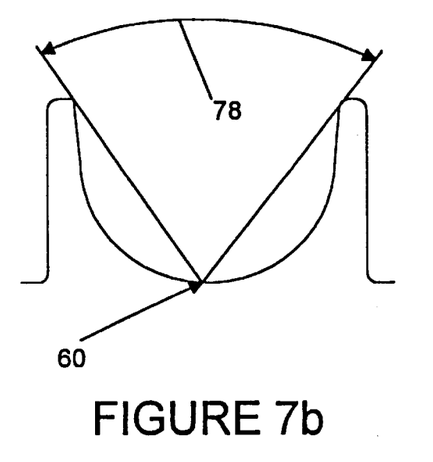
FIG. 7b is a minor axis side cross-sectional view of this reservoir.

In contrast to FIGS. 5*a–b* and 6*a–b* (prior art), FIGS. 7*a–b* (again depicting x-y and z-y cross sections, similar to the illustrations of FIGS. 3, 3*a,* and 4) illustrates the full delivery/removal access angle range 78 and the true low point 60 which the present inventive dilution reservoir 10 provides. A user may easily dispense and remove contents of the cavities 38 without always rigidly approaching at a single angle, like a well, and in fact a very wide access angle range 78 is provided. This access range 78 extends to either side of vertical, unlike the range 76 in FIGS. 6*a–b*. The wide access range 78 makes the dilution reservoir 10 easy to use as well as inherently more forgiving (i.e., a user need not hold a dispensing device, like a pipettor, perfectly rigid). This, in turn, reduces awkwardness when manipulating individual samples, and over periods of time, when dealing with large numbers of samples, also reduces repetitive stress ergonomic concerns.

In addition to the above mentioned examples, various other modifications and alterations of the inventive dilution reservoir 10 may be made without departing from the invention. Accordingly, the above disclosure is not to be considered as limiting and the appended claims are to be interpreted as encompassing the true spirit and the entire scope of the invention.

Indistrial Applicability

The present dilution reservoir 10 is well suited for any scientific or clinical procedure that might have been performed with conventional dilution reservoirs of either the well type or the trough type reservoir as have existed heretofore. It is especially useful in laboratory applications where multiple samples of material are being manipulated with a standard laboratory pipettor. The improved design allows easier access of material into the channels 30 and their respective cavities 38 through the mouths 40.

Typically, samples are loaded into the channels 30 of the dilution reservoir 10 together with solvents and reagents, which might be necessary for the procedure. The width of the channel mouths 40 in the transverse axis 48 dimension and the thickness of the central barriers 50 have been designed so that a multichannel pipettor with standard tip to tip spacing of 9 mm can easily be inserted. The elongation of the mouths 40 in the longitudinal axis 44 dimension allows the pipettor to be inserted in a wide range of access angles 78. This is very advantageous to the user who may have to perform this operation many times in the course of a day. This will lead to an improvement in efficiency, and accuracy may be improved as spillage is reduced due to improved ease of pipettor alignment. User fatigue will be decreased and reduction in repetitive stress complaints can be expected.

The larger volume of the cavities 38, together with the elongation of the channels' mouths 40, allow easier insertion of mixing devices such as a pipette. This increased volume allows room for manipulation of the mixing device and thus promotes easier and more complete mixing of the reservoir 10 contents.

The unique arcuate cross-sectional profile of the dilution reservoir 10 provides a true low point 60 in the bottom 56 of each cavity 38 as seen in both longitudinal axis 44 and transverse axis 48 cross-sectional views. This greatly facilitates complete and efficient removal of the reservoir 10 contents. Increased experimental accuracy can be obtained in applications where it is important that retention of residue in a reservoir be minimized or eliminated. Also, a decrease in processing time can be expected if material can be collected and manipulated more efficiently.

The disposable nature of the dilution reservoirs 10 can also make processing more efficient in facilities with high numerical requirements by eliminating the need to clean and sterilize vessels between uses. In addition, the stackable nature of the reservoirs 10 allow for decreased storage space, both before and after use, as well as in supply storage houses. Also, the cover 12 provided can be useful in preventing spillage and evaporation of volatile contents, as well as reduction in contamination of reservoir materials.

For the above, and other, reasons, it is expected that the dilution reservoir 10 of the present invention will have widespread industrial applicability. Therefore, it is expected that the commercial utility of the present invention will be extensive and long lasting.

What is claimed is:

1. A dilution reservoir, comprising:
    a housing, having:
        abase,
        a top opposite said base, and
        a plurality of sides;
    a plurality of channels located in said housing each said channel having:
        a channel mouth opening at the top of said housing,
        a transverse axis,
        a longitudinal axis, such that said channels are longer along said longitudinal axis than along said transverse axis, wherein said plurality of channels are disposed parallel to each other along said longitudinal axis, and
        a depth axis; and
    said channels having arcuate cross-sections, as seen in cross-sections taken along both said transverse axis and said longitudinal axis.

2. A dilution reservoir as in claim 1, wherein:
said channels are spaced with 9mm between centers of said channel mouths to allow easy introduction of the dispensing tips of a standard multichannel pipettor.

3. A dilution reservoir as in claim 1, wherein:
said parallel channels are grouped in multiples.

4. A dilution reservoir as in claim 3, wherein:
the number of multiples is a variable selected from the group consisting of 2, 3, 4, 6, 8 and 12.

5. A dilution reservoir as in claim 1, wherein:
said mouths of said parallel channels are off-set as a group toward one of said plurality of sides thus providing room on said top of said housing for optional information marking.

6. A dilution reservoir as in claim 1, wherein:
said arcuate cross-sections of said channels are sections of circles.

7. A dilution reservoir as in claim 6, wherein:
said sections of circles are semi-circles.

8. A dilution reservoir as in claim 1, wherein:
said arcuate cross-sections of said channels are sections of ellipses.

9. A dilution reservoir as in claim 1, wherein:
said arcuate cross-sections of said channels are parabolic.

10. A dilution reservoir as in claim 1, wherein:
said dilution reservoir is made with the spacing of channels and housing sides such that said dilution reservoir is stackable.

11. A dilution reservoir as in claim 1, wherein:
said dilution reservoir is disposable.

12. A dilution reservoir as in claim 1, further comprising:
a removable cover.

13. A dilution reservoir as in claim 1, wherein:
said housing further includes a flared extension formed on said base of said housing to provide stability.

* * * * *